(12) United States Patent
Sowinski et al.

(10) Patent No.: US 7,955,373 B2
(45) Date of Patent: Jun. 7, 2011

(54) TWO-STAGE STENT-GRAFT AND METHOD OF DELIVERING SAME

(75) Inventors: Krzysztof Sowinski, Wallington, NJ (US); Ronald Rakos, Nesmanic Station, NY (US); Dennis Kujawski, Warwick, NY (US); Patrice K. Nazzaro, Hoboken, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1350 days.

(21) Appl. No.: 10/878,241

(22) Filed: Jun. 28, 2004

(65) Prior Publication Data

US 2005/0288768 A1 Dec. 29, 2005

(51) Int. Cl.
*A61F 2/82* (2006.01)
(52) U.S. Cl. ...................................... 623/1.13
(58) Field of Classification Search .............. 623/1.13, 623/1.15, 1.16
See application file for complete search history.

(56) References Cited

U.S. PATENT DOCUMENTS

| | | | |
|---|---|---|---|
| 3,986,828 A | 10/1976 | Hoffman, Jr. et al. | |
| 4,304,010 A | 12/1981 | Mano | |
| 4,503,569 A | 3/1985 | Dotter | |
| 4,580,568 A | 4/1986 | Gianturco | |
| 4,732,152 A | 3/1988 | Wallstén et al. | |
| 4,733,665 A | 3/1988 | Palmaz | |
| 4,886,062 A | 12/1989 | Wiktor | |
| 5,061,276 A | 10/1991 | Tu et al. | |
| 5,064,435 A * | 11/1991 | Porter ........................... | 623/23.7 |
| 5,123,917 A | 6/1992 | Lee | |
| 5,133,742 A | 7/1992 | Pinchuk | |
| 5,178,630 A | 1/1993 | Schmitt | |
| 5,192,310 A | 3/1993 | Herweck et al. | |
| 5,209,776 A | 5/1993 | Bass et al. | |
| 5,229,431 A | 7/1993 | Pinchuk | |
| 5,549,860 A | 8/1996 | Charlesworth et al. | |
| 5,665,114 A | 9/1997 | Weadock et al. | |
| 5,700,285 A | 12/1997 | Myers et al. | |
| 5,713,917 A * | 2/1998 | Leonhardt et al. .............| 606/194 |
| 5,735,892 A | 4/1998 | Myers et al. | |
| 5,741,332 A | 4/1998 | Schmitt | |
| 5,749,880 A | 5/1998 | Banas et al. | |
| 5,800,512 A | 9/1998 | Lentz et al. | |
| 5,817,126 A * | 10/1998 | Imran ........................... | 623/1.15 |
| 5,851,229 A | 12/1998 | Lentz et al. | |
| 5,916,264 A * | 6/1999 | Von Oepen et al. ......... | 623/1.15 |
| 5,925,075 A | 7/1999 | Myers et al. | |
| 5,928,279 A | 7/1999 | Shannon et al. | |
| 5,948,018 A | 9/1999 | Dereume et al. | |
| 5,993,489 A | 11/1999 | Lewis et al. | |

(Continued)

FOREIGN PATENT DOCUMENTS

WO  WO 01/67993 A  9/2001

(Continued)

*Primary Examiner* — Ryan J Severson

(74) *Attorney, Agent, or Firm* — Brooks, Cameron & Huebsch, PLLC

(57) ABSTRACT

A stent-graft is provided for defining a prosthetic fluid passage within a body lumen. The stent-graft includes a graft having a forward section, and a pilot stent located within the forward section of the graft. The pilot stent has an expanded diameter less than that of a lumen in which it is to be deployed to permit fluid flow within the lumen during deployment of the stent-graft. Means are provided for subsequently expanding the pilot stent and the graft to the full diameter of the lumen.

20 Claims, 6 Drawing Sheets

U.S. PATENT DOCUMENTS

| | | | |
|---|---|---|---|
| 6,001,125 A | 12/1999 | Golds et al. | |
| 6,015,431 A | 1/2000 | Thornton et al. | |
| 6,036,724 A | 3/2000 | Lentz et al. | |
| 6,039,755 A | 3/2000 | Edwin et al. | |
| 6,080,198 A | 6/2000 | Lentz et al. | |
| 6,090,137 A | 7/2000 | Schmitt | |
| 6,123,723 A | 9/2000 | Konya et al. | |
| 6,165,212 A | 12/2000 | Dereume et al. | |
| 6,221,099 B1 | 4/2001 | Andersen et al. | |
| 6,344,054 B1 | 2/2002 | Parodi | |
| 6,368,347 B1 | 4/2002 | Maini et al. | |
| 6,428,571 B1 | 8/2002 | Lentz et al. | |
| 6,440,166 B1 | 8/2002 | Kolluri | |
| 6,514,283 B2 | 2/2003 | DiMatteo et al. | |
| 6,517,571 B1 | 2/2003 | Brauker et al. | |
| 6,524,334 B1 | 2/2003 | Thompson | |
| 6,540,773 B2 | 4/2003 | Dong | |
| 6,547,815 B2 | 4/2003 | Myers | |
| 6,547,820 B1 | 4/2003 | Staudenmeier | |
| 6,554,855 B1 | 4/2003 | Dong | |
| 6,585,758 B1 | 7/2003 | Chouinard et al. | |
| 6,652,580 B1 | 11/2003 | Chuter et al. | |
| 6,716,239 B2 | 4/2004 | Sowinski et al. | |
| 6,719,783 B2 | 4/2004 | Lentz et al. | |
| 6,770,087 B2 | 8/2004 | Layne et al. | |
| 2002/0010505 A1* | 1/2002 | Richter | 623/1.15 |
| 2002/0038142 A1* | 3/2002 | Khosravi et al. | 623/1.13 |
| 2002/0120327 A1* | 8/2002 | Cox et al. | 623/1.16 |
| 2002/0165601 A1* | 11/2002 | Clerc | 623/1.13 |
| 2003/0009210 A1 | 1/2003 | Sowinski et al. | |
| 2003/0017775 A1 | 1/2003 | Sowinski et al. | |
| 2003/0082323 A1 | 5/2003 | Venditti et al. | |
| 2003/0082324 A1 | 5/2003 | Sogard et al. | |
| 2003/0114918 A1* | 6/2003 | Garrison et al. | 623/1.13 |
| 2003/0139806 A1 | 7/2003 | Haverkost et al. | |
| 2003/0204241 A1 | 10/2003 | Dong | |
| 2004/0033364 A1 | 2/2004 | Spiridigliozzi et al. | |

FOREIGN PATENT DOCUMENTS

WO  WO 2004/017867 A   3/2004

* cited by examiner

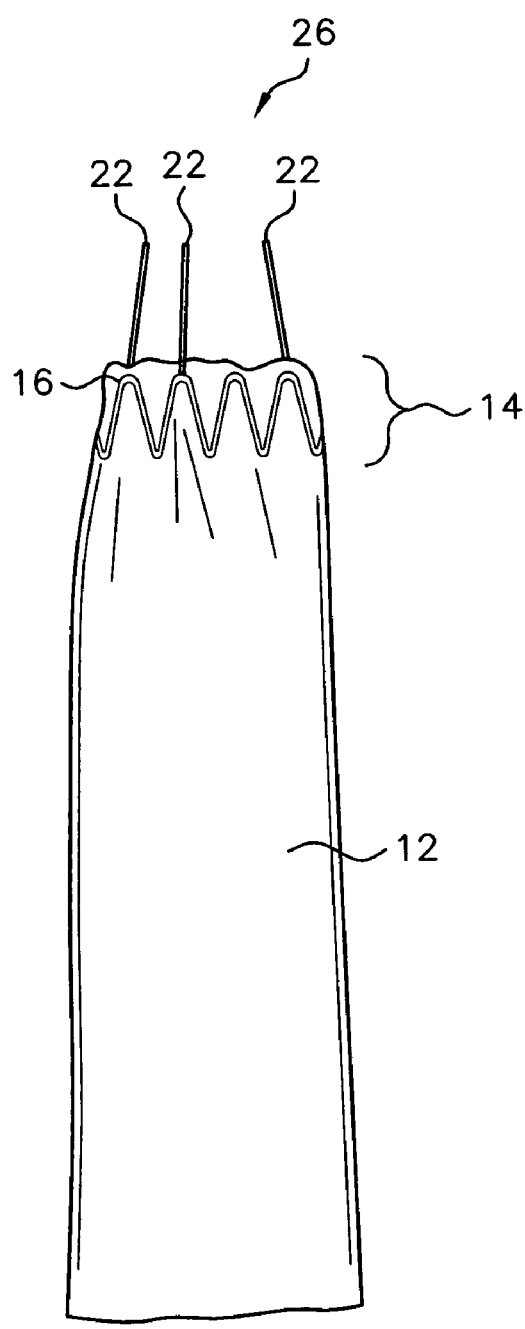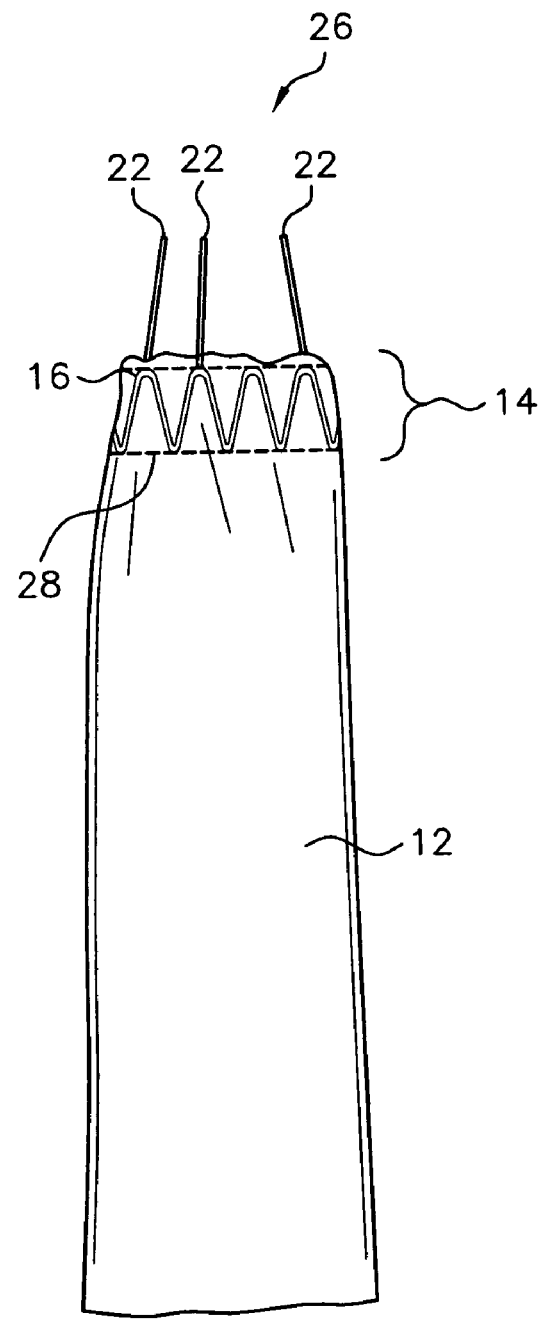
FIG. 2A  FIG. 2B

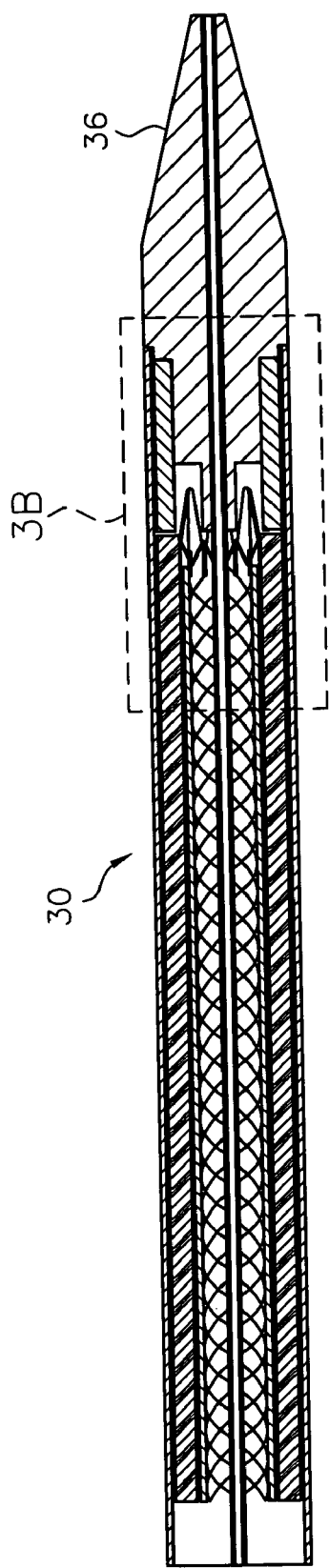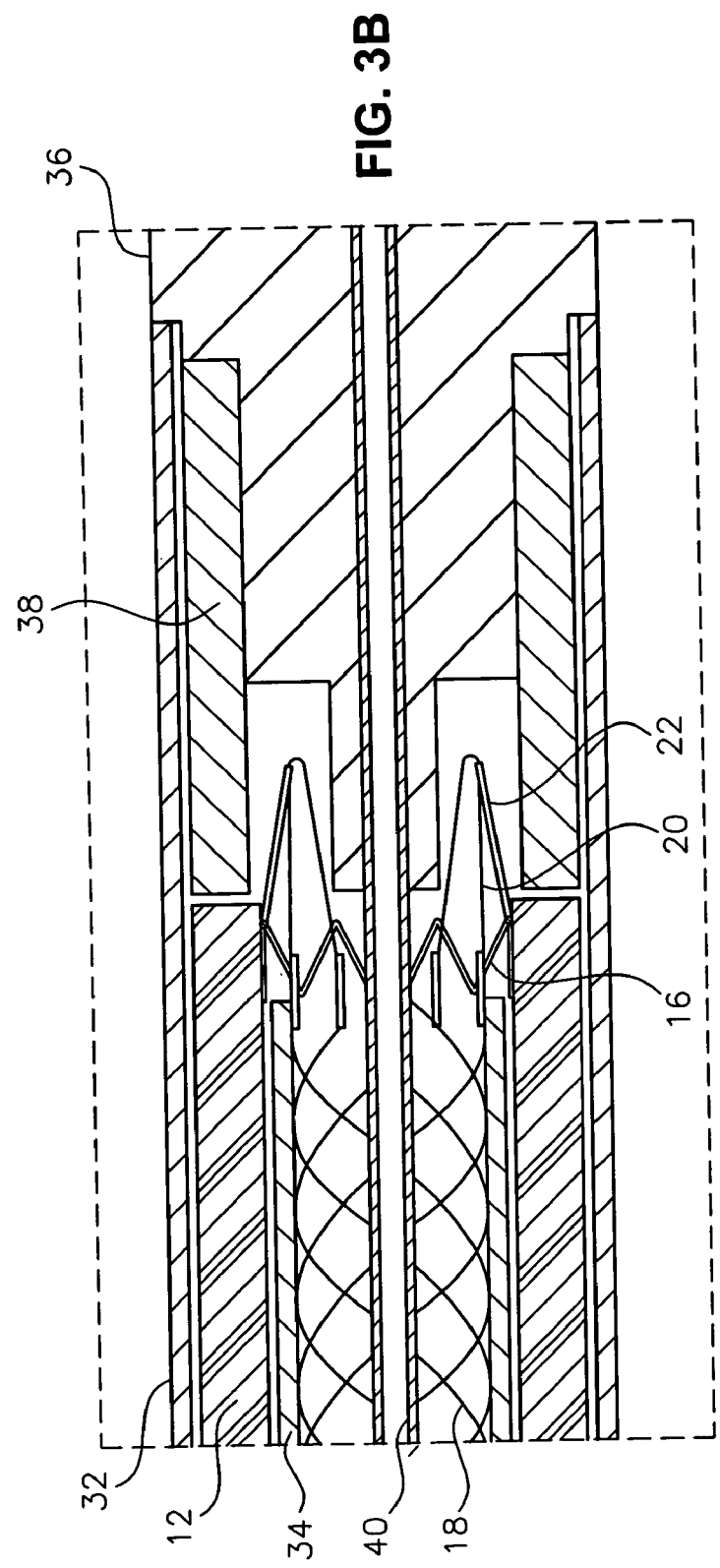

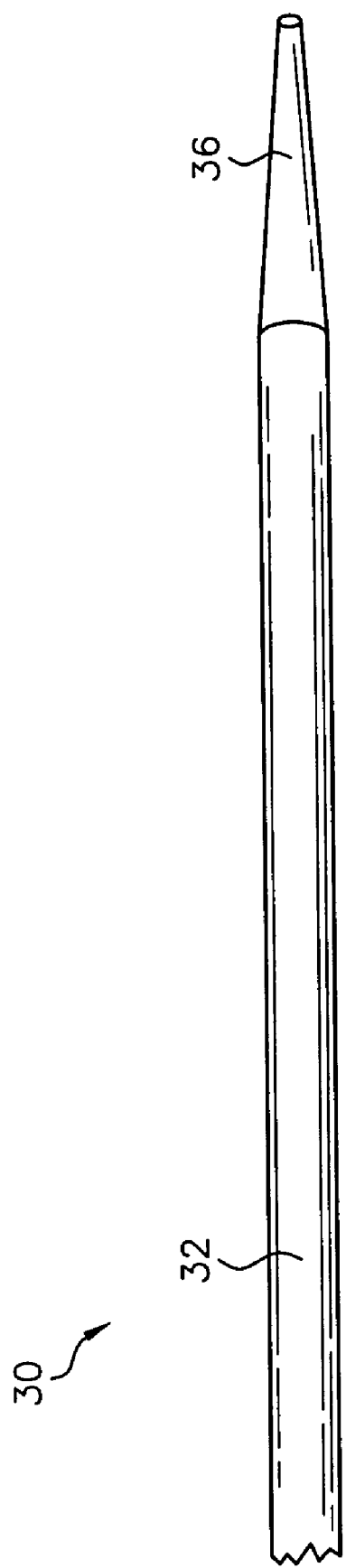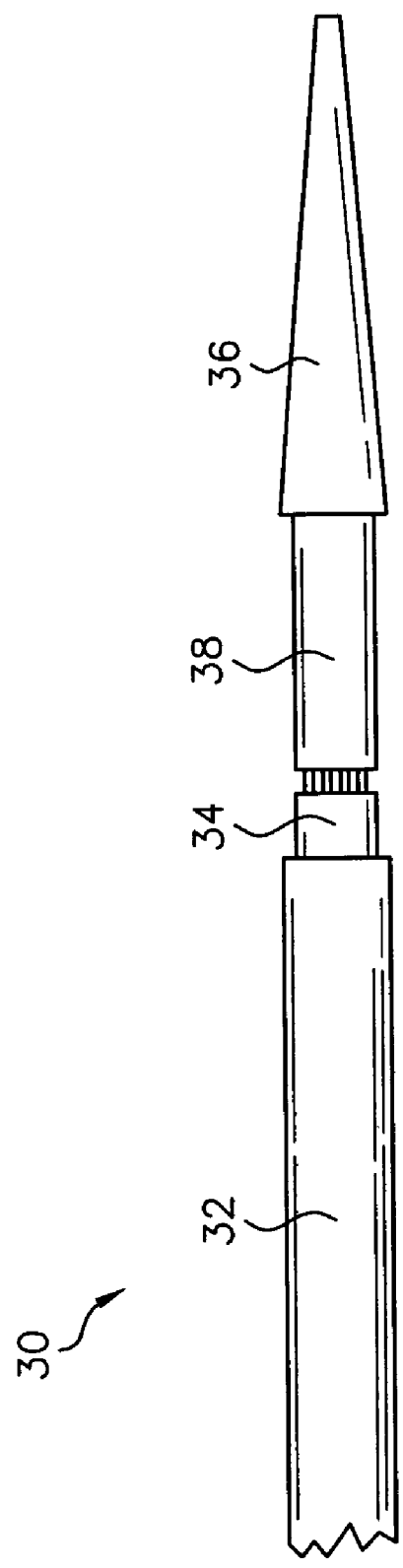

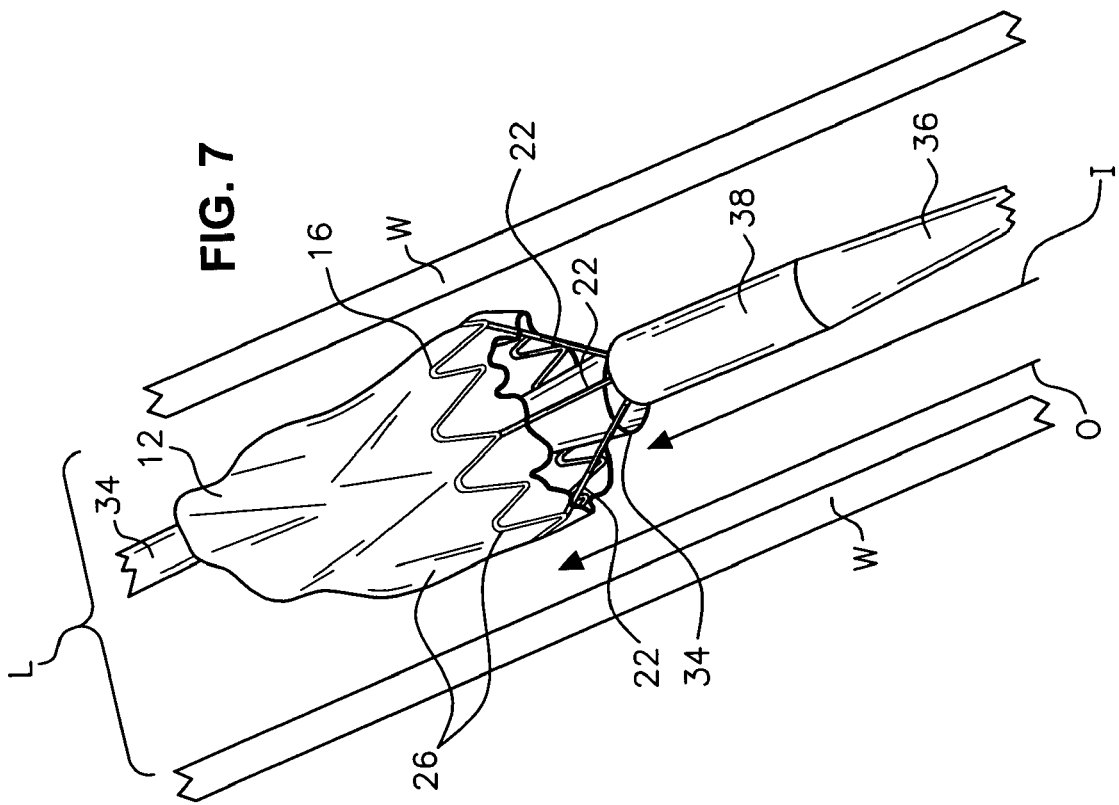
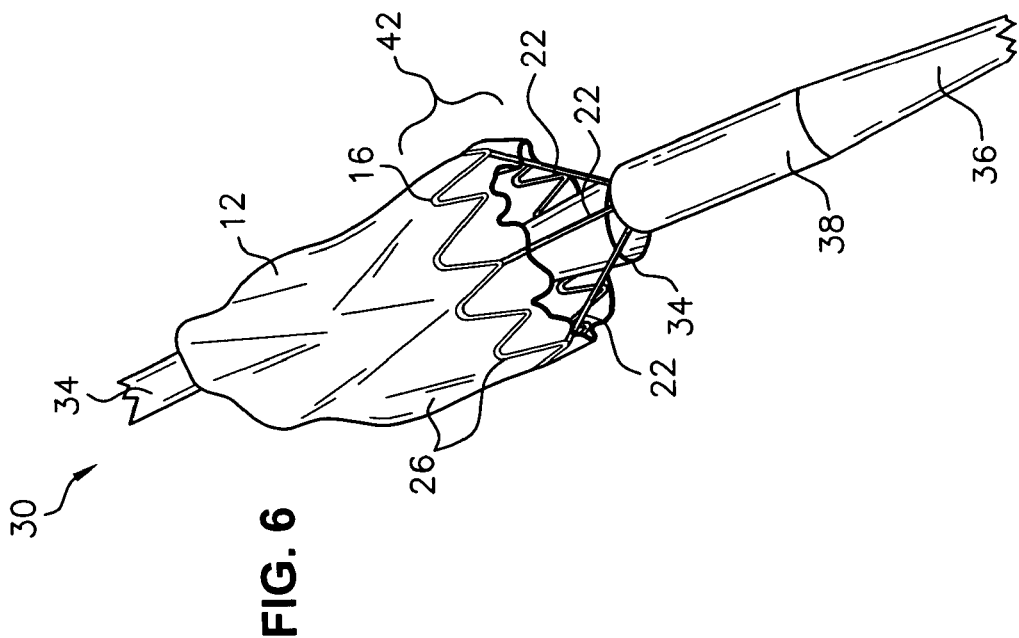

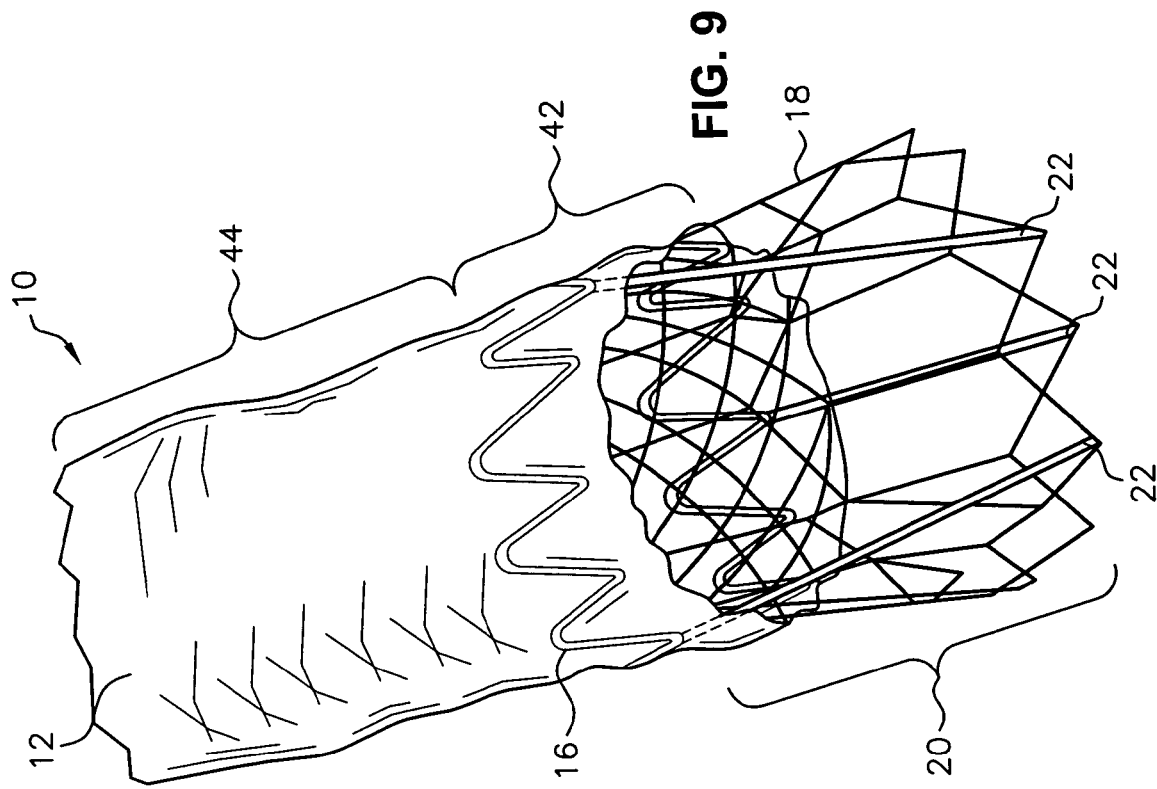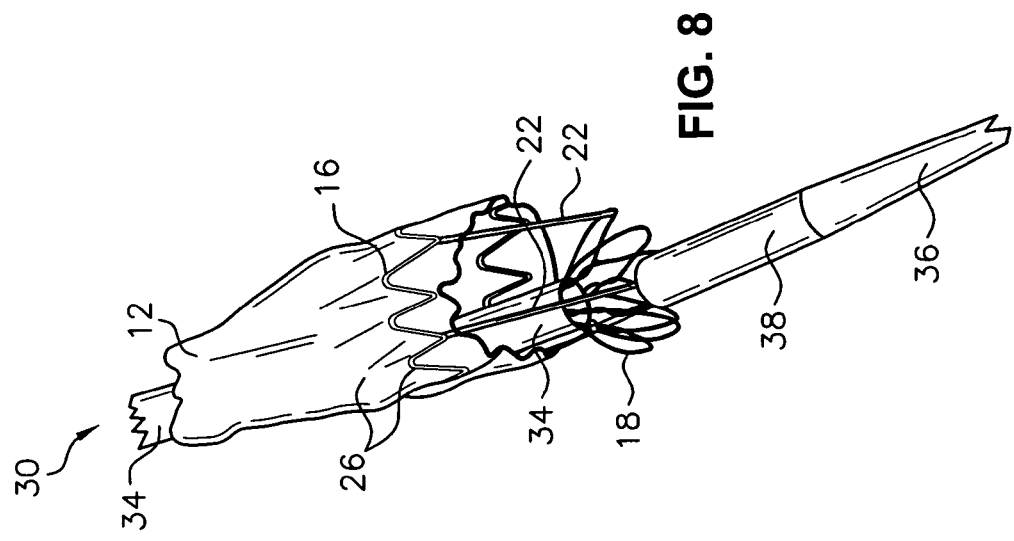

TWO-STAGE STENT-GRAFT AND METHOD OF DELIVERING SAME

FIELD OF THE INVENTION

The present invention relates to a stent-graft for defining a fluid passage within a body lumen. More specifically, the present invention relates to a stent-graft adapted for endoluminal deployment with minimal disruption of fluid flow through the lumen.

BACKGROUND OF THE INVENTION

A stent-graft is typically used to provide a prosthetic intraluminal wall, e.g., in the case of a vascular stenosis or aneurysm, to provide an unobstructed conduit for blood in the area of the stenosis or aneurysm. A stent-graft may be endoluminally deployed in a body lumen, a blood vessel for example, at the site of a stenosis or aneurysm by so-called "minimally invasive techniques" in which the stent-graft is compressed radially inwards and is delivered by a catheter to the site where it is required, through the patient's skin, or by a "cut down" technique at a location where the blood vessel concerned is accessible. When the stent-graft is positioned at the correct location, the stent-graft is caused or allowed to re-expand to a predetermined diameter in the vessel.

Accurately positioning a stent-graft prior to deployment can present challenges, e.g., impaired blood flow. Furthermore, deployment of a stent-graft within a thoracic aorta (ascending aorta) brings about added maneuverability and placement challenges of higher blood flow rate and pressure as compared to lower flow and pressure conditions within an abdominal aorta (descending aorta). For these and other reasons, improvements in stent-grafts to facilitate deployment with less disruption of fluid flow during deployment would be of significant utility.

SUMMARY OF THE INVENTION

According to one aspect of this invention, a stent-graft is provided for defining a fluid passage within a body lumen comprising a native fluid passageway. The stent-graft includes a graft having a forward section, and a pilot stent located within the forward section of the graft. The pilot stent has an initial expanded is diameter less than that of a lumen in which it is to be deployed to permit fluid flow within the lumen during deployment of the stent-graft. The stent-graft further includes a main stent located within the graft and having a forward section located within the pilot stent. The main stent has an expanded diameter approximating that of the body lumen. Both the pilot stent and the main stent have a compressed diameter for delivery endoluminally. A member connects the pilot stent to the main stent. The graft is attached only to the pilot stent.

According to another aspect of this invention, a two-stage stent-graft delivery system is provided. The two-stage stent-graft delivery system includes a pilot stent-graft comprising a pilot stent and a tubular graft. The two-stage stent-graft delivery system further includes an outer sheath surrounding the pilot stent-graft, a main stent deployed within the pilot stent-graft, and an inner sheath surrounding the main stent within the pilot stent-graft. One or more members connect the pilot stent-graft to the main stent. A tip surrounds a distal end of the main stent, and a small sheath is attached to the tip and surrounds the distal end of the main stent. The pilot stent-graft is adapted, upon rearward movement of the outer sheath, to expand the pilot stent to an outer diameter less than that of a lumen in which it is to be deployed, and to permit the graft to expand to permit fluid flow therethrough and therearound. The main stent is adapted to be deployed upon rearward movement of the inner sheath and thereby to expand the pilot stent and the graft to the full diameter of the lumen.

According to yet another aspect of this invention, a method of delivering a two-stage stent-graft is provided. A delivery system including the two-stage stent-graft is positioned in a desired location within a lumen. An outer sheath is retracted, thereby permitting a pilot stent to expand a leading edge of a tubular graft to an outer diameter less than that of a lumen in which it is deployed and permitting the graft to expand. A tip is advanced to partially deploy a distal end of a main stent. An inner sheath is retracted, thereby permitting the main stent to expand the pilot stent, the leading edge of the tubular graft, and a main body of the tubular graft to a full diameter of the lumen. The delivery system is then removed.

In all embodiments, a pilot stent is deployed first so that fluid flow in the native passageway of the lumen continues around the pilot stent and graft, but also begins to flow through the pilot stent and the forward end of the graft (located upstream in the passageway) which then opens like a windsock to permit fluid flow therethrough. Thereafter the graft is expanded to the full diameter of the lumen in which it is deployed.

BRIEF DESCRIPTION OF THE DRAWINGS

FIG. 2A is a view of a pilot stent-graft including connecting members in accordance with an embodiment of the present invention;

FIG. 2B is a view of a pilot stent-graft including connecting members in accordance with another embodiment of the present invention;

FIG. 3A is a schematic cross-sectional view of a two-stage stent-graft delivery system in accordance with the present invention;

FIG. 3B is an exploded view of one section of the two-stage stent-graft delivery system represented in FIG. 3A;

FIG. 4 is view of the two-stage stent-graft delivery system represented in FIG. 3A in its initial, pre-delivery configuration, showing a tip surrounded by an outer sheath;

FIG. 5 is a view of the two-stage stent-graft delivery system illustrated in FIG. 4 showing the outer sheath in a retracted position;

FIG. 6 is a perspective view of the two-stage stent-graft delivery system illustrated in FIGS. 3A, 3B and 4 during delivery, showing a deployed pilot stent-graft including connecting members tucked under a small sheath connected to the tip;

FIG. 7 is a perspective view of the two-stage stent-graft delivery system illustrated in FIG. 6 representing diagrammatically a lumen in which the stent-graft is deployed and the direction of fluid flow therethrough;

FIG. 8 is a perspective view of the two-stage stent-graft delivery system illustrated in FIG. 6 showing the tip moved forward to partially deploy the main stent; and FIG. 9 is a perspective view of the same stent-graft in its fully deployed configuration.

DETAILED DESCRIPTION OF THE INVENTION

Figure 1:
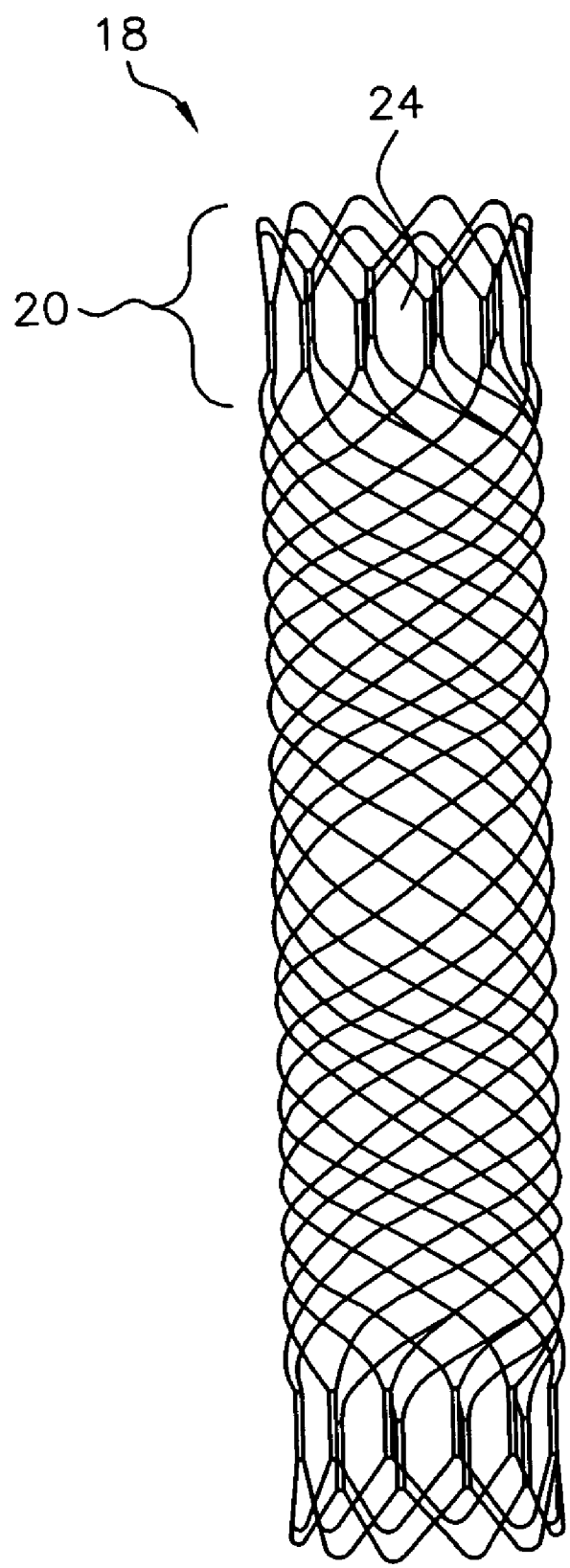
FIG. 1 is a view of a stent which may be used in accordance with the present invention.

Although the invention is illustrated and described herein with reference to specific embodiments, the invention is not intended to be limited to the details shown. Rather, various modifications may be made in the details within the scope and range of equivalents of the claims and without departing from the invention.

Referring generally to FIGS. 1-9, there is shown a stent-graft 10 for defining a prosthetic fluid passage within a body lumen "L." Stent-graft 10 includes a graft 12 having a forward section 14, and a pilot stent 16 located within forward section 14 of graft 12. Pilot stent 16 has an expanded initial diameter less than that of a lumen "L" in which it is to be deployed to permit fluid flow within lumen "L" during deployment of stent-graft 10. Stent-graft 10 further includes a main stent 18 located within graft 12 and having a forward section 20 located just forward of, but at least partially within, pilot stent 16. Main stent 18 has an expanded diameter approximating that of body lumen "L." Both the pilot stent 16 and the main stent 18 have a compressed diameter for delivery endoluminally. The pilot stent 16 will be expanded to its final diameter (that of the lumen "L") upon deployment of the main stent 18. Members 22 connect pilot stent 16 to main stent 18. Graft 12 is attached only to pilot stent 16. It may be attached by laminating or bonding.

An exemplary material for forming graft 12 is expanded polytetraflouroethylene. The present invention, however, is not limited to polytetraflouroethylene, and may include textile, composite textile structure (hybrid fabric), or any other material that offers the desired properties of graft 12 and that is suitable for affixation to pilot stent 16. One suitable material is that described in U.S. application Ser. No. 10/166,842 filed Jun. 11, 2002, entitled, "COMPOSITE ePTFE/TEXTILE PROSTHESIS," which is incorporated herein by reference.

Affixation of graft 12 to pilot stent 16 may include bonding material (adhesive or otherwise), sutures, metal clips, staples, or any combination thereof, for example. Pilot stent 16 may be affixed to either an inside surface or an outside surface of graft 12.

Alternatively, the graft may comprise a laminate and the pilot stent 16 may be positioned between layers of the laminate. For example, an inner layer of expanded polytetraflouroethylene and an outer layer of fabric may include a pilot stent 16 sandwiched between the layers and affixed with an adhesive such as Corethane or polycarbonate urethane. Similarly, the pilot stent 16 may be laminated between two layers of expanded polytetraflouroethylene or between a graft and a circumferential band of material adhered to the graft. The circumferential band of material may form the inner layer, or the outer layer, depending upon the desired construction. The various laminated layering configurations may be reinforced with sutures, metal clips, staples, or any combination thereof. In summary, multiple layers of various textile, composite textile structure (hybrid fabric), and expanded polytetraflouroethylene constructions may be utilized that offer the desired properties of graft 12 and that are suitable for affixation to pilot stent 16.

Referring specifically to FIG. 1, a straight, tubular main stent 12 is illustrated. Main stent 12 is self-expanding, and is adapted to expand within a body lumen "L" (represented in FIG. 7) in which it is deployed. As illustrated, in this embodiment, each end of main stent 12 comprises hexagonal openings 24, which remain uncovered when the stent-graft 10 is fully deployed. Alternatively, main stent 12 may include looped ends, or any other desired end configuration that is self-expanding. Furthermore, the present invention is not limited to a straight tubular stent, and may include a tapered tubular stent or any other shaped stent that is self-expanding, with or without uncovered ends.

Main stent 18 is located within a pilot stent-graft 26 (illustrated in FIGS. 2A and 2B). Referring specifically to FIGS. 2A and 2B and the pilot stent-graft 26, graft 12 has a forward section 14, and a pilot stent 16 located within forward section 14 of graft 12. Pilot stent 16 is self-expanding, and has an expanded diameter less than that of a lumen "L" in which it is to be deployed to permit fluid flow within lumen "L" during deployment of stent-graft 10 (as illustrated in FIG. 7). As illustrated, pilot stent 16 is zig-zag shaped. Alternatively, the shape of pilot stent 16 may comprise hexagonally open cells or any other configuration that is self-expanding. Optionally, the material of pilot stent 16 is made of, or coated with, a radiographically differentiable material to facilitate placement of the device with radiographic imaging.

Both pilot stent 16 and main stent 18 have a compressed diameter for delivery endoluminally. As will be discussed subsequently herein, graft 12 is adapted to be expanded first by pilot stent 16, then by fluid flowing through graft 12, and lastly by main stent 18.

FIGS. 2A and 2B illustrate connecting members 22 attached to pilot stent 16. Members 22 connect pilot stent 16 to main stent 18 (illustrated in FIGS. 8 and 9). Members 22 may comprise wire material. Other materials may be used as well, however, and may comprise, for example, conventional suture material, expanded polytetraflouroethylene, or other flexible material strong enough to sustain the connection. As will be discussed subsequently herein, members 22 are preferably comprised of a material having sufficient column strength to maintain pilot stent 16 and main stent 18 longitudinally fixed relative to each other. In the embodiment of FIGS. 2A, 2B, and 6-9, three members 22 are included. The present invention, however, is not limited to three members, and may include any number of members suitable for attaching pilot stent 16 to main stent 18.

Pilot stent 16, as shown in FIGS. 2A and 2B, is represented in phantom lines to illustrate that it is covered by graft 12, or the outer layer of graft 12 for embodiments in which graft 12 comprises a laminate. FIG. 2A illustrates those embodiments which graft 12 is attached to pilot stent 16 via bonding either alone or in combination with a laminate between the layers of which pilot stent 16 is sandwiched. FIG. 2B illustrates an embodiment in which pilot stent 16 is sandwiched between an outer layer of fabric (or expanded polytetraflouroethylene) and an inner band 28 of material adhered to the graft.

FIGS. 3A and 3B are schematic cross-sectional views illustrating the relationship between the components of the two-stage stent-graft delivery system 30 in accordance with the present invention, prior to deployment. As represented, the two-stage stent-graft delivery system 30 includes an outer sheath 32 surrounding pilot stent-graft 26, in turn surrounding main stent 18, and an inner sheath 34 disposed between main stent 18 and pilot stent-graft 26. As explained previously herein, members 22 connect pilot stent-graft 26 to main stent 18. A tip 36 surrounds a distal end 20 of main stent 18, and a small sheath 38 is attached to tip 36 and surrounds distal end 20 of main stent 18. Optionally, small sheath 38 and tip 36 may comprise one molded part. A central member 40 acts as a guide wire lumen and as a pusher for tip 36 to facilitate the operation of the two-stage stent-graft delivery system 30.

Pilot stent-graft 26 is adapted, upon rearward movement of outer sheath 32, to expand pilot stent 16 to an outer diameter less than that of a lumen "L" (represented in FIG. 7) in which it is to be deployed, permitting graft 12 to be expanded by pilot stent 16 to permit fluid flow. Main stent 18 is adapted to be deployed upon rearward movement of inner sheath 34, thereby expanding pilot stent 16 and graft 12 to the full diameter of the lumen "L."

FIG. 4 is an outer view of the two-stage stent-graft delivery system 30 represented in FIG. 3A in its initial, pre-delivery configuration, showing tip 36 surrounded by outer sheath 32. It is at this stage that the two-stage stent-graft delivery system 30 is positioned in a desired location within a lumen "L" (represented in FIG. 7). FIG. 5 illustrates the two-stage stent-graft delivery system 30, at the beginning of the deployment procedure, showing outer sheath 32 in a partially retracted position, thereby exposing the entire tip 36 and small sheath 38, and a portion of inner sheath 34.

Referring to FIG. 6, the two-stage stent-graft delivery system 30 is shown during its first stage of delivery. Outer sheath 32 has been retracted completely, thereby permitting pilot stent 16 to deploy, partially deploying graft 12. More specifically, pilot stent 16 expands a leading edge 42 of tubular graft 12 to an outer diameter less than that of a lumen "L" (represented in FIG. 7) in which it is deployed, and permits graft 12 to expand prior to deployment of main stent 18. At this stage, main stent 18 resides within inner sheath 34 and small sheath 38. Members 22 connect pilot stent 16 to main stent 18, which is currently hidden from view underneath small sheath 38.

In FIG. 7, the exemplary configuration of the two-stage stent-graft delivery system 30 illustrated in FIG. 6 is shown relative to a representative lumen "L" in which it is deployed and fluid flow "I" and "O." More specifically, pilot stent 16 is holding graft 12 open within lumen "L" in a windsock fashion. Fluid "I" can flow inside graft 12, and fluid "O" can flow outside graft 12, helping to ensure steady fluid flow through lumen "L" during deployment of main stent 18. Such constant fluid flow enables main stent 18 to be slowly and carefully deployed, ensuring accurate placement. Furthermore, by enabling steady fluid flow through lumen "L," the windsock configuration aids the maneuverability of stent-graft 10 even when exposed to the relatively high blood flow rate and pressure of a thoracic aorta (ascending aorta) for which this embodiment is intended.

Referring to FIG. 8, the two-stage stent-graft delivery system 30 is shown during its second stage of delivery. Throughout the delivery process, members 22 maintain pilot stent 16 and main stent 18 fixed relative to each other. In other words, members 22 constrain longitudinal movement and prevent pilot stent-graft 26 from floating downstream via blood flow "I" and "O."

At this stage, tip 36 is advanced to partially deploy forward end 20 of main stent 18. Fluid can continue to flow freely inside "I" graft 12 and outside "O" graft 12 (as represented in FIG. 7), and it can also flow through the wires of the partially opened forward end 20 of main stent 18. The radiographically differentiable material of pilot stent 16 can be clearly seen via fluoroscopy, and since fluid is flowing freely around and within graft 12, the two-stage stent-graft delivery system 30 can be easily maneuvered for accurate placement. If it is determined that main stent 18 is positioned incorrectly, it can be recaptured by extending inner sheath 34 forward toward tip 36. The two-stage stent-graft delivery system 30 may then be repositioned accordingly.

When it is determined that main stent 18 is positioned in the desired location, inner sheath 34 is retracted completely, thereby permitting main stent 18 to expand pilot stent 16, leading edge 42 of tubular graft 12, and a main body 44 of tubular graft 12 to a full diameter (as represented in FIG. 9) of lumen "L." In other words, graft 12 is trapped between the lumen "L" or vessel wall "W" (as represented in FIG. 7), and main stent 18. At all times, fluid can flow through the wires of main stent 18 and inside graft 12.

The present invention is not limited to the sequence of delivery stages described previously herein with reference to FIGS. 6-10. For example, subsequent to the first stage of delivery of the two-stage stent-graft delivery system 30 as illustrated in FIG. 6 (where the outer sheath 32 has been retracted completely, thereby permitting pilot stent 16 to deploy, partially deploying graft 12), the second stage of delivery (previously represented in FIG. 8) may include retracting completely inner sheath 34. Such a step permits, at this stage, main stent 18 to expand pilot stent 16, leading edge 42 of tubular graft 12, and a main body 44 of tubular graft 12. Tip 36 is then advanced to deploy forward end 20 of main stent 18, and the two-stage stent-graft delivery system 30 is expanded to a full diameter (as represented in FIG. 9) of lumen "L."

The delivery system, including central member 40, is then removed. FIG. 9 illustrates the delivered stent-graft 10.

The foregoing embodiment is particularly adapted for placement in a large blood vessel such as the thoracic artery and particularly adapted for placement with the forward, uncovered ends of the main stent at the intersection of the main vessel with branches thereof so that fluid flow to or from the branches is not impeded.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A stent-graft for defining a prosthetic fluid passage within a body lumen comprising a native fluid passageway, said stent-graft comprising:
    a tubular graft having a forward section configured to be located upstream in the body lumen;
    a pilot stent located within said forward section of said tubular graft configured to have a fully self-expanded diameter, after deployment independent of a main stent, that is less than that of the body lumen to permit fluid flow within the body lumen during deployment of said stent-graft; and
    said main stent located within said tubular graft and having a forward section located forward of said pilot stent and at least partially radially within said pilot stent,
    said main stent extending rearward of said pilot stent,
    said main stent having an expanded diameter approximating that of the body lumen,
    both said pilot stent and said main stent having a compressed diameter for delivery endoluminally,
    said pilot stent being configured to independently expand with respect to said main stent to the diameter that is less than that of the body lumen;
    said tubular graft being attached to said pilot stent and configured to be free to expand to permit fluid therethrough and therearound when said pilot stent is expanded and said main stent is not yet deployed; and
    said main stent being configured to expand said pilot stent and said tubular graft to a full diameter of the body lumen after being deployed.

2. The stent-graft as recited in claim 1, wherein said pilot stent is attached to said main stent.

3. The stent-graft as recited in claim 2, wherein said attachment comprises one or more wires.

4. The stent-graft as recited in claim 2, wherein said attachment comprises one or more lines of suture material.

5. The stent-graft as recited in claim 2, wherein said attachment comprises a plurality of members extending from a forward end of said pilot stent and connecting to a forward end of said main stent.

6. The stent-graft as recited in claim 1, wherein the material of said tubular graft is expanded polytetraflouroethylene.

7. The stent-graft as recited in claim 1, wherein the material of said tubular graft is fabric.

8. The stent-graft as recited in claim 1, wherein said tubular graft comprises at least two layers of material.

9. The stent-graft as recited in claim 8, wherein said pilot stent is secured between said layers of material.

10. The stent-graft as recited in claim 1, further comprising an inner band of material located within said pilot stent and cooperating with said tubular graft to attach said pilot stent to said tubular graft.

11. The stent-graft as recited in claim 1, wherein said pilot stent is a self-expanding zig-zag stent.

12. The stent-graft as recited in claim 11, wherein said main stent is a self-expanding mesh with hexagonal opening at its forward end.

13. The stent-graft as recited in claim 1, wherein said main stent is a self-expanding mesh with hexagonal openings at its forward end.

14. The stein-graft as recited in claim 1, wherein said pilot stent is radiographically imagable.

15. The stent-graft as recited in claim 1, wherein said stent-graft is configured to be deployed in a lumen with side branches, said main stent includes a forward section, forward of said pilot stent and of the forward end of said graft, and said stent-graft is configured to be deployed with the forward section of said main stent where the side branches intersect the lumen.

16. The stent-graft according to claim 1, wherein the pilot stent is not integrally formed with the main stent.

17. The stent-graft according to claim 1, wherein the pilot stent has a self-expanded diameter less than that of a body lumen in which is it to be deployed.

18. A stent-graft for defining a prosthetic fluid passage within a body lumen, said stent-graft comprising:
   a tubular graft;
   a pilot stent located at a forward section of said tubular graft; and
   a main stent located within the tubular graft, the main stent being not integrally formed with the pilot stent, said main stent having a forward section located forward of said pilot stent and at least partially radially within said pilot stent, said main stent extending rearward of said pilot stent;
   both said pilot stent and said main stent having a compressed diameter for delivery endoluminally, said pilot stent being configured to independently expand with respect to said main stent from the compressed diameter of the pilot stent, and said tubular graft being attached to said pilot stent and being configured to be free to expand to permit fluid therethrough and therearound when said pilot stent is expanded from the compressed diameter of the pilot stent to a fully self-expanded diameter and said main stent is not yet expanded from the compressed diameter of the main stent.

19. The stent graft according to claim 18, wherein the main stent includes a forward section located radially within the pilot stent.

20. The stent-graft according to claim 18, wherein said main stent is attached to said pilot stent by a plurality of members extending from a forward end of said pilot stent and connecting to a forward end of said main stent.

* * * * *